United States Patent [19]

Biss et al.

[11] Patent Number: 5,177,113
[45] Date of Patent: Jan. 5, 1993

[54] FREE-STANDING, POROUS FOAM PVP:$H_2O_2$ PRODUCT

[75] Inventors: Russell B. Biss, Wayne; Jeffrey M. Cohen, Fanwood; John J. Merianos, Middletown; Paul D. Taylor, West Milford, all of N.J.

[73] Assignee: ISP Investments Inc., Wilmington, Del.

[21] Appl. No.: 883,617

[22] Filed: Mar. 4, 1992

Related U.S. Application Data

[63] Continuation-in-part of Ser. No. 721,786, Jun. 26, 1991, abandoned.

[51] Int. Cl.$^5$ .................... A61K 31/79; A61K 33/40; A61K 47/38
[52] U.S. Cl. .................... 514/772.5; 424/78.24; 424/405; 424/616; 514/781
[58] Field of Search .................... 574/772.5; 424/78.24

[56] References Cited

U.S. PATENT DOCUMENTS 3,480,557  11/1969  Shiraeff .................... 252/186
4,769,013  9/1988  Lorenz et al. .................... 604/265

Primary Examiner—Thurman K. Page
Assistant Examiner—Neil Levy
Attorney, Agent, or Firm—Walter Katz; Marilyn J. Maue; Joshua J. Ward

[57] ABSTRACT

A free-standing, porous foam product comprising an integral network of PVP molecules hydrogen-bonded to $H_2O_2$ molecules, optionally including a water-soluble gelling agent; e.g. hydroxyethyl cellulose; in an amount up to 60% by weight of the product, its PVP content being about 25–90% by weight of the product, and the $H_2O_2$ content being about 5–24% by weight. In the absence of a gelling agent, the product has a bulk density of about 0.3 to about 0.5 g/cc and a porosity of about 60–70%. When a gelling agent is present in the product, its bulk density and porosity of the product is substantially reduced and, accordingly, it has a more foam-like structure and appearance.

3 Claims, No Drawings

FREE-STANDING, POROUS FOAM PVP:H$_2$O$_2$ PRODUCT

CROSS-REFERENCE TO RELATED PATENT APPLICATION

This application is a continuation-in-part of copending U.S. patent application Ser. No. 721,786, filed Jun. 26, 1991, now abandoned, and assigned to the same assignee as herein.

BACKGROUND OF THE INVENTION

1. Field of the Invention

This invention relates to a free-standing, porous foam product comprising an integral network of polyvinylpyrrolidone (PVP) molecules hydrogen-bonded to hydrogen peroxide (H$_2$O$_2$) molecules, and to a method of making such products.

2. Description of the Prior Art

Stabilized H$_2$O$_2$ compositions have found wide utility in commercial and industrial applications, e.g. as antiseptics, disinfectants, sterilization agents, bleaching materials, washing concentrates, etchants, in cosmetic preparations, as cigarette filters, and as a catalyst in polymerizations requiring a free radical source. In biological applications which require an antiseptic, disinfectant or sterilization agent, such H$_2$O$_2$ compositions require release of an effective amount of oxygen at a desired rate.

Shiraeff, in U.S. Pat. Nos. 3,376,110 and 3,480,557, prepared various compositions of PVP and H$_2$O$_2$ by mixing an aqueous solution of PVP and a substantial excess of H$_2$O$_2$, and evaporating the solution to dryness at 90–100° C. The H$_2$O$_2$ content of the compositions obtained, however, was quite variable, ranging from 2% to 70% by weight, and considerable water was present in the final composition. Prolonged drying of the composition, in an attempt to reduce its water content, resulted in a further loss of H$_2$O$_2$. The resultant product was described as a brittle-film, or a transparent, gummy, amorphous material.

Merianos, in U.S. Pat. No. 5,008,093, provided free-flowing, stable, high purity, substantially anhydrous powders of PVP and H$_2$O$_2$ in defined molar ratios of 1:1 or 2:1. These free-flowing products were made by reacting a suspension of PVP and a solution of H$_2$O$_2$ in an anhydrous organic solvent, such as ethyl acetate. The free-flowing PVP-H$_2$O$_2$ powders made by Merianos represented a significant advance in this art because the peroxide content was reproducible.

Biss, in U.S. Pat. No. 5,077,047, described a commercial process for the production of such free-flowing powders wherein a fluidized bed of PVP powders was maintained at a reaction temperature of from ambient to 60° C. and contacted with finely-divided droplets of an aqueous H$_2$O$_2$ solution containing about 30 to 85% by weight hydrogen peroxide. The resultant product was a stable, substantially anhydrous, free-flowing powder of 1:1 molar ratio PVP-H$_2$O$_2$.

Rainer, in U.S. Pat. No. 4,182,743, described a filter material for selective removal of aldehydes from cigarette smoke which consisted of a gas-permeable substrate or carrier, such as silica gel, on which a film of a composition of concentrated H$_2$O$_2$, PVP and water was formed. The film was made by applying an aqueous solution of H$_2$O$_2$ and PVP onto the carrier material, and drying in a vacuum oven or desiccator at room temperature.

These and other methods described in the art, however, have not provided a free-standing, porous foam product of PVP and H$_2$O$_2$, optionally including a water-soluble gelling agent, by freeze-drying an aqueous solution of H$_2$O$_2$ and PVP, optionally with the gelling agent, and removing the water under predetermined process conditions which enable the formation of such a free-standing, porous foam product.

SUMMARY OF THE INVENTION

This invention provides a free-standing, porous foam product comprising an integral network of PVP molecules hydrogen-bonded to H$_2$O$_2$ molecules, optionally including a water-soluble gelling agent therein. The PVP content of the product suitably is about 20–90% by weight, the H$_2$O$_2$ content is about 5–24% by weight, and the gelling agent, e.g. hydroxyethyl cellulose, comprises up to 60% by weight, of the product.

The free-standing, porous foam products of the invention are made by freeze-drying an aqueous solution of PVP and H$_2$O$_2$, and removing water at a temperature below −20° C. and at a reduced pressure of less than about 0.1 mm.

In the absence of a gelling agent, the foam product has a bulk density of about 0.3 to about 0.5 g/cc and a porosity of about 60–70%; when a water-soluble gelling agent is present, e.g. in an amount of about 20–60%, the bulk density and porosity is substantially lower.

DETAILED DESCRIPTION OF THE INVENTION

In accordance with the present invention, the starting PVP polymer material can be provided as a water-soluble polymer having a molecular weight corresponding to a Fikhenser K-value of from K-15 to K-90. These PVP polymers, which generally have a water content of about 5% by weight, or less, and a particle size of about 10 to 100 microns, may be used directly in the process of the invention, or pre-dried, if desired, to further reduce its moisture content. The aqueous hydrogen peroxide solution used herein usually contains about 5 to 10% hydrogen peroxide, although higher and lower concentrations may be used as well.

In one embodiment of the invention, an aqueous solution of PVP and H$_2$O$_2$ is prepared containing about 4–10% by weight of H$_2$O$_2$, about 15–25% by weight of PVP, and about 65–85% by weight of water. Most preferably, the aqueous solution of PVP and H$_2$O$_2$ contains about 6% H$_2$O$_2$, 20% PVP and 74% water.

The aqueous solution thus obtained then is frozen at a temperature of less than −20° C. to form a soft ice of the desired product. The soft ice then is vacuum dried at low temperatures under high vacuum, preferably, at about 0.1 mm or less, whereupon water is removed from the material and is condensed in a suitable condenser maintained at about −90° C.

The freeze-drying step is carried out for some period of time; thereupon, water leaves the interior of the ice body and a free-standing, porous foam is formed whose chemical structure comprises an open, integral network of PVP molecules hydrogen-bonded to H$_2$O$_2$ molecules. During transition of the soft ice into the porous foam, a tacky material is observed in which some water is retained on the outer surfaces of the body. However, by keeping this intermediate material well-dispersed and cold, the exterior water present can be readily removed by vacuum-sublimation to provide the desired porous foam product.

The final product in this embodiment is a free-standing, porous foam composed of an integral network of about 70-90% by weight PVP which is hydrogen-bonded to about 10-24% by weight $H_2O_2$, and where the amount of water present therein is less than 10%. Preferably, the PVP content of this product is about 75-85%, the amount of $H_2O_2$ is about 15-20%, and its water content is less than about 7½%. Suitably, the total amount of $H_2O_2$ and water therein is about 25% or less by weight of the product. Most preferably, PVP is 77-82%, $H_2O_2$ is 17-19% and water is about 2-7½%.

The product has a bulk density of about 0.3 to about 0.5 g/cc and a porosity of about 60-70%.

In another embodiment of the invention, a water-soluble gelling agent is incorporated within the porous foam during formation to increase its porosity. Suitable gelling agents include hydroxyalkyl cellulose e.g. hydroxyethyl cellulose, propylene and ethylene glycols, polyalkylene glycols, and the like. The resultant porous foam product then comprises about 25-70% PVP, 5-20% $H_2O_2$, about 20-60% gelling agent; and 0-8% water, by weight of the product.

The invention herein also contemplates the formation of compositions, or mixtures, of the porous solid PVP-$H_2O_2$ product herein admixed with diluents, carriers, or other active materials. For example, an improved filter material may be provided by forming admixtures of the PVP-$H_2O_2$ product of the invention with such diluents as inorganic substances such as silica gel, alumina, diatomaceous earth and the like, or organic substances such as polyolefins, polystyrene, polyvinyl chloride and the like, while retaining the desirable pore volume of the porous solid complex. The resultant pore volume of such mixtures for filter application should be between about 0.1 and 2.5 cc per granular of total granular material.

The invention will be illustrated now by reference to the following examples.

EXAMPLE 1

An aqueous solution of PVP/hydrogen peroxide was prepared by mixing 20 parts by weight of polyvinylpyrrolidone (K-30) with 80 parts by weight of a 7.6 weight % aqueous hydrogen peroxide solution. The solution was then cooled to a temperature below $-20°$ C. whereupon a solid was formed. This solid material was then cryogenically ground while its temperature remained below $-20°$ C. by prechilling a grinder and grinding the frozen solution with dry ice. The granulated material then was charged into a prechilled vacuum jar. A high vacuum of <0.1 mm Hg was applied to the contents while maintaining the jar in a chilled bath at $<-20°$ C. A condenser element was maintained at $-95°$ C. to freeze out any moisture before entering the vacuum pump. After 28 hours, nearly all of the water in the solid was removed leaving a porous solid at room temperature containing 15-18% hydrogen peroxide, 3-4½% water, and the remainder PVP.

EXAMPLE 2

The procedure of Example 1 was followed except that the aqueous solution was frozen into pieces 2-3 inches thick, and then vacuum dried while in the chilled state. The resulting material was a foam with a bulk density of about 0.43 g/cc and a porosity of 66%. This foam material had a hydrogen peroxide content of 17½%, and a moisture content of 7½% after 48 hours of vacuum drying under the same conditions as in Example 1.

EXAMPLE 3

90 parts of an aqueous solution of 20% polyvinylpyrrolidone (PVP C-30/CI grade) and 6% hydrogen peroxide were mixed with 10 parts of hydroxyethyl cellulose (HEC) and allowed to gel for 20 to 30 minutes. The gelled material had an overall composition of: 18.0% PVP, 10.0% HEC, 5.4% $H_2O_2$, and 66.6% water. The material then was placed in a freeze-dryer at ambient temperature and evacuated to about 0.1 mm Hg for about 18 hours. The resulting solid retained a volume similar to the initial gel, however, the water loss had reduced the sample to 32% of its original weight. Analysis of the product showed a composition as follows: 55.2% PVP, 30.7% HEC, 12.8% $H_2O_2$ and 1.3% water.

While the invention has been described with particular reference to certain embodiments thereof, it will be understood that changes and modifications may be made which are within the skill of the art. Accordingly, it is intended to be bound only by the following claims.

What is claimed is:

1. A process for making a free-standing, porous foam product which consist essentially of PVP molecules hydrogen bonded to $H_2O_2$ molecules, optionally including a water-soluble gelling agent, the PVP content being about 20-90% by weight, the $H_2O_2$ content being about 5-24% by weight, about 20-60% by weight of a gelling agent, and about 0-8% water by weight, the bulk density being about 0.3-0.5 g/cc or less, and the porosity being about 60-70%, or less, if the gelling agent is present, which comprises
   (a) providing an aqueous solution containing PVP, $H_2O_2$, optionally a gelling agent, and water, in amounts of PVP, $H_2O_2$ and gelling agent to provide said product after processing,
   (b) freezing the aqueous solution at below about $-20°$ C. to form a soft ice, and
   (c) vacuum drying the soft ice at a reduced pressure of less than about 0.1 mm to remove water therefrom.

2. A process according to claim 1 wherein water is removed by sublimation from the soft ice and condensed at about $-90°$ C.

3. A process according to claim 1 wherein the aqueous solution includes hydroxyethyl cellulose as a water-soluble gelling agent.

* * * * *